United States Patent [19]

Diana

[11] Patent Number: 4,538,010

[45] Date of Patent: Aug. 27, 1985

[54] ALCOHOL RECOVERY PROCESS

[75] Inventor: William D. Diana, Belle Mead, N.J.

[73] Assignee: Exxon Research & Engineering Co., Florham, N.J.

[21] Appl. No.: 650,874

[22] Filed: Sep. 17, 1984

[51] Int. Cl.[3] ........................ C07C 29/86; C07C 31/12

[52] U.S. Cl. .................................... 568/918; 568/886; 568/888; 568/889

[58] Field of Search .......................... 568/918, 888–890

[56] References Cited

U.S. PATENT DOCUMENTS

| | | | |
|---|---|---|---|
| 1,954,506 | 4/1934 | Van Peski et al. | 568/889 |
| 2,081,721 | 5/1937 | Van Dijck et al. | 568/918 |
| 2,109,462 | 3/1938 | Burk et al. | 568/888 |
| 2,196,177 | 4/1940 | Burk et al. | 568/918 |
| 2,510,806 | 6/1950 | Egberts et al. | 568/918 |
| 2,535,069 | 12/1950 | Johnson | 568/918 |
| 3,527,790 | 9/1970 | Moundlic et al. | 568/889 |

FOREIGN PATENT DOCUMENTS

| | | | |
|---|---|---|---|
| 334228 | 9/1930 | United Kingdom | 568/889 |
| 411303 | 6/1934 | United Kingdom | 568/889 |
| 830369 | 3/1960 | United Kingdom | 568/889 |

OTHER PUBLICATIONS

Roddy, Ind. Eng. Chem. Proc. Des. Dev., vol. 20, No. 1, pp. 104–108 (1981).

*Primary Examiner*—J. E. Evans
*Attorney, Agent, or Firm*—Jack B. Murray, Jr.

[57] ABSTRACT

According to the process of this invention, saturated mono-alcohols are recovered from solutions containing such mono-alcohols together with a carboxylic acid extraction solvent therefor by passing the mono-alcohol solution to an alcohol vaporization zone, introducing a substantially anhydrous stripping gas to the alcohol vaporization zone in an amount and under conditions sufficient to form vapors comprising the mono-alcohol and to form an alcohol-depleted liquid phase comprising the carboxylic acid extraction solvent.

30 Claims, 3 Drawing Figures

ALCOHOL RECOVERY PROCESS

CROSS-REFERENCE TO RELATED APPLICATION

This application is related to application Ser. No. 650,875, entitled "Improved Process for Recovering Alcohols from Sulfuric Acid Streams", filed on even date herewith.

BACKGROUND OF THE INVENTION

1. Field of the Invention

This invention relates generally to the recovery of alcohols from concentrated aqueous acid streams.

2. Description of the Prior Art

Large volumes of alcohols are produced annually by the catalytic hydration of olefins, in which the selected olefin feed is absorbed in a concentrated aqueous sulfuric acid stream to form the corresponding alcohol and alkyl ester of the sulfuric acid. For example, the absorption of butene to form sec-butanol and a sec-butyl ester of sulfuric acid can be illustrated by the following equation:

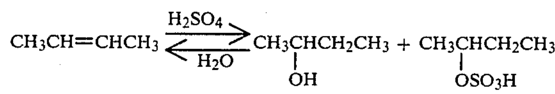

Thereafter, water is admixed with the sulfuric acid stream withdrawn from the absorber to hydrolyze the ester and to facilitate alcohol recovery which is accomplished by stripping with steam. There is thereby produced a diluted sulfuric acid stream which must for economic reasons be treated to concentrate it with respect to its sulfuric acid content, after which it is recycled to the olefin absorption step.

The reconcentration of the diluted sulfuric acid stream is a very expensive and energy-intensive process step, and a method whereby the alcohol could be recovered from the sulfuric acid stream withdrawn from the absorber, which did not require such a reconcentration, would be highly desirable.

Processes have been proposed for alcohol recovery by extraction from such alcohol-containing sulfuric acid streams by use of benzene, chloroform, ether, carbon bisulfide and toluene (U.S. Pat. No. 1,365,046); phenols, cresols, their homologues, ethers and phosphates (U.S. Pat. No. 2,139,953); and saturated hydrocarbons (British Pat. No. 493,884). British Pat. No. 506,473 relates to a method for production of organic oxy-compounds from a mixture of two liquid phases containing the oxy-compound distributed between the two layers in which the layers are separated and then recontacted at a lower temperature to extract the oxy-compound from the more hydrophobic phase, e.g., a hydrocarbon phase.

However, such extraction methods are not commercially desirable, since the solvents extract very little alcohol if the acid strength of the alcohol-containing sulfuric acid stream is greater than about 55%. Dilution of the acid stream to improve the ability of these solvents to extract the alcohol is not economically practicable, since even more expense would be incurred in reconcentrating the resulting sulfuric acid (recovered after the extraction) prior to its being recycled to the olefin absorbing step.

C. L. Munson et al., Ind. Eng. Chem. Proc. Des. Dev., vol. 23, no. 1, pp. 109–115 (1984) (which is not admitted herein to be prior art) investigated equilibrium distribution coefficients and separation factors for extraction of ethanol from dilute aqueous solutions of the alcohol by a number of different solvents and solvent mixtures, including extraction solvents comprising neodecanoic acid and 2-ethyl hexanoic acid. An ethanol-water-extraction solvent phase is obtained and treated to dehydrate the ethanol, followed by fractionating the ethanol and solvent mixture. The dilute aqueous raffinate is separated from the extractor and treated, as by stripping, to separate extraction solvent dissolved in the raffinate.

SUMMARY OF THE INVENTION

According to the process of this invention, saturated mono-alcohols are recovered from solutions containing such mono-alcohols together with a carboxylic acid extraction solvent therefor by passing the mono-alcohol solution to an alcohol vaporization zone, introducing a substantially anhydrous stripping gas to said alcohol vaporization zone in an amount and under conditions sufficient to form vapors comprising the mono-alcohol and to form an alcohol-depleted liquid phase comprising the carboxylic acid extraction solvent.

The mono-alcohol containing solutions which can be treated by the above method are preferably obtained by extraction of the mono-alcohol from aqueous-strong acid solutions of the alcohol using as extraction solvent a carboxylic acid selected from the group consisting of acids of the formula $RCO_2H$ wherein R is a straight or branched chain or cyclic alkyl of from 5 to 19 carbon atoms, as discussed in co-pending application Ser. No. 650,875, entitled "Improved Process for Recovering Alcohols from Sulfuric Acid Streams", the disclosure of which is hereby incorporated by reference.

It has been surprisingly found that open steam distillation or steam stripping of such alcohol-containing carboxylic acid extraction solvent solutions results in a liquid phase from the stripping step in which the carboxylic acid extraction solvent contains significant levels of water, which is undesired in subsequent use of the carboxylic acid extraction solvent as recycled to an extraction zone in which the mono-alcohol is sought to be removed from such aqueous-strong acid solutions. Therefore, while the advantages of open steam injection (such as outstanding heat transfer capacity between the open steam, the alcohol sought to be vaporized, compatibility of the alcohol and steam, cheap and readily available sources of steam and steam injection apparatus, and the like) would make this method the first choice of one seeking to recover the alcohol vapors, its disadvantage of passing significant levels of water to the liquid phase recovered from such a stream stripping zone are unexpected and unacceptably large.

The alcohol removal process of this invention thereby provides further efficiencies and removal of the alcohol from concentrated aqueous-strong acid solutions thereof in which in the first step the strong acid solution is contacted with the carboxylic acid extraction solvent to efficiently recover the alcohol in a resulting carboxylic acid extract phase which in addition to the alcohol contains substantially no water and substantially no strong acid contamination. In the second step, the alcohol is recovered by treatment in a vaporization zone according to the method of this invention to form an alcohol-depleted carboxylic acid extraction solvent liquid which can then be recycled to the extraction zone.

DETAILED DESCRIPTION OF THE INVENTION

Prior Art Methods

Figure 1:
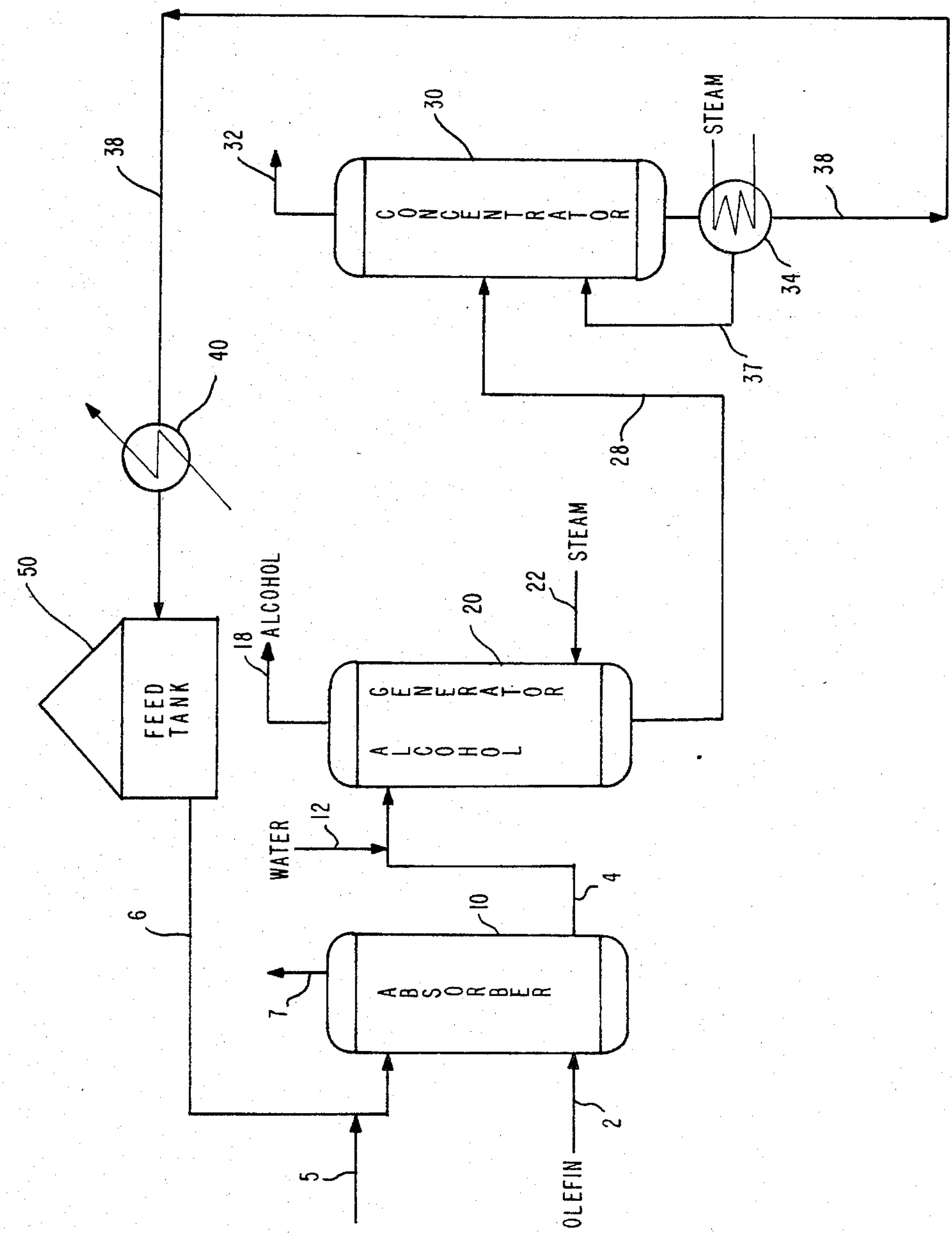
FIG. 1 is a diagrammatic illustration of a prior art process for indirect hydration of olefins using sulfuric acid, dilution of the sulfuric acid extract and stream stripping of the diluted acid for recovery of the alcohol vapors.

The prior art method of producing alcohols by hydrating the corresponding olefin can be illustrated by reference to FIG. 1. An olefin, for example an aliphatic olefin having from 2 to 8, and more typically from 2 to 4, carbon atoms per molecule (e.g., ethylene, propylene or butylene) is fed as a gas or liquid via line 2 to an absorber 10 wherein it is contacted with and absorbed (at least in part) by a concentrated aqueous strong acid stream introduced via line 6, to form the corresponding alcohol and alkyl ester of the strong acid.

The olefins to be hydrated can be obtained from any available source, such as the destructive distillation of carbonaceous materials, but particularly from the cracking of petroleum hydrocarbons such as is practiced in the petroleum refining of mineral oils. The olefin can also be conventionally obtained by careful fractionation of cracked petroleum gases and is preferably substantially free of higher unsaturates, particularly diolefins such as butadiene, etc. Illustrative of olefins which are employed are lower branched and straight-chain alkenes (i.e., alkenes of 2 to 6 carbon atoms), such as ethylene, propylene, the butylenes and the like.

The strong acid used to absorb the olefin in absorber 10 (also termed "olefin hydration acid") will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like. For convenience, the following discussion will be directed to the use of sulfuric acid, although it will be understood that any of the above strong acids could also be employed.

The aqueous strong acid stream 6 which is used to absorb the selected olefin feed is a concentrated acid stream whose precise acid concentration will vary depending on the olefin which is employed, the strong acid selected, the temperatures of reaction and other conditions. For example, when sulfuric acid is used as the strong acid, stream 6 will generally contain from about 45 to 99% acid strength sulfuric acid for hydration of propylene and from about 55 to 85% acid strength sulfuric acid for reaction with butylene or higher olefin feeds.

The temperature and pressure employed in absorber 10 generally also varies depending on the olefin, the acid concentration and other factors. Generally, a temperature of from about 20° to 150° C. is used, and the pressure is sufficient to maintain the desired liquid phases in the absorber. Typically, for example, propylene is absorbed from a gas phase at a temperature of from about 90° to 150° C., and at a pressure of from about 100–500 psig.

As illustrated, the olefin and sulfuric acid streams are contacted in a counter-current fashion with the sulfuric acid stream being introduced into the upper portion of the absorber 10. Unabsorbed gases are withdrawn from the upper portion of absorber 10 via conduit 7 and can be recycled, if desired, to conduit 2 or can be subjected to conventional scrubbing/washing treatment, as with caustic solutions. A product stream, comprising a sulfuric acid solution of the alcohol (herein termed the "absorber product stream"), is withdrawn via line 4 from the lower portion of absorber 10. The absorber product stream can also contain the alkyl ester corresponding to the selected olefin, e.g., diethyl sulfate when ethylene is the olefin, and di-(isopropyl) sulfate in the case of propylene hydration. The concentration of the alkyl ester in stream 4 can vary widely, and is generally from 15 to 30 wt. % of the total alkyl ester (mono- and di-alkyl ester) in the case of lower alkenes (e.g., propylene and butylene) absorption.

In the second step of the hydration process, water is conventionally added via line 12 to the absorber product stream 4 for hydrolysis of any alkyl ester and to form additional quantities of the corresponding alcohol, e.g., isopropanol from mono- or di-(isopropyl) sulfate. The manner in which the water and absorber product stream are contacted varies, and the art employs a variety of such methods, including (1) in-line addition of water (as illustrated), with a provision for a suitable length of conduit to provide adequate mixing and reaction time, and (2) contacting of the absorber product stream and water in a separate reaction vessel with agitation (not shown).

The amount of water which is added to the absorber product stream also varies widely. Generally, sufficient water is added in order to reduce the acid strength to from 45% to 55% sulfuric acid. These reduced acid strengths are desired to permit subsequent recovery of the alcohol by steam stripping. Typically, from about 0.2 to 0.5 parts by weight of water is added per part by weight of the absorber product stream.

The diluted stream thus formed generally contains from about 45 to 55 wt. % sulfuric acid, and is then passed via line 4 to distillation column 20, herein termed the "alcohol generator," wherein crude alcohol is recovered as an overhead product via line 18 by steam stripping. The overhead alcohol product can then be passed to further conventional processing to produce alcohol of the required purity.

A bottoms product is withdrawn from alcohol generator 20 via line 28 and comprises a sulfuric acid stream which generally contains from about 40 to 55 wt. % sulfuric acid.

In conventional processes, the alcohol generator bottoms 28 are passed directly to another distillation column 30, hereinafter termed the "acid concentrator", wherein this acid stream is distilled (e.g., by use of a steam heat exchanger 34 and reboiled stream 37) for removal of water as overhead 32 and to form a second bottoms product 38 comprising a reconcentrated acid stream. These concentrated bottoms are generally cooled in cooler 40 and passed to storage tank 50 for ultimate recycle to the absorption step 10, with addition of make-up acid 5, as required.

PRESENT INVENTION

Figure 2:
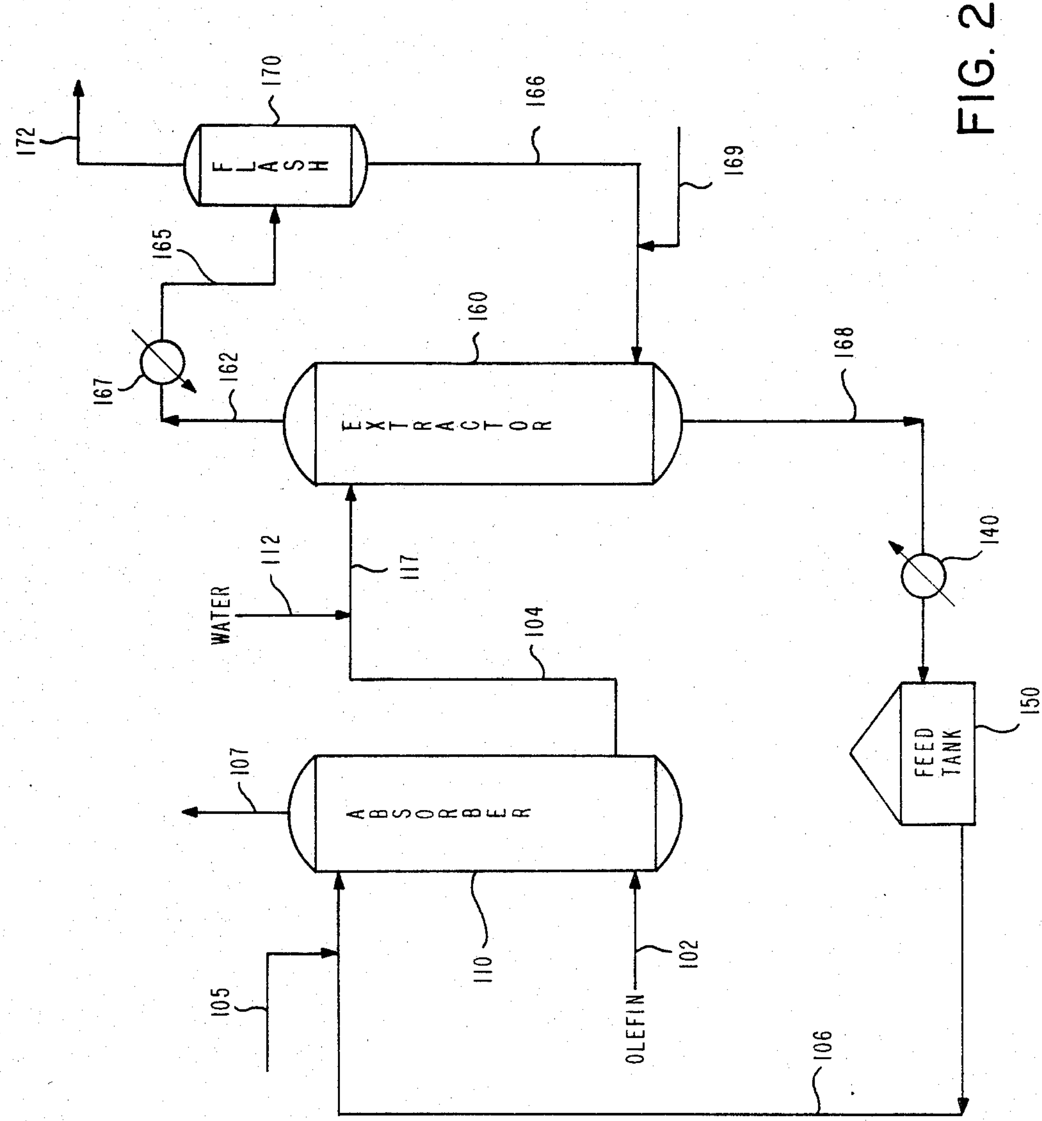
FIG. 2 is a diagrammatic illustration of one embodiment of the cyclic process of this invention.

Referring to FIG. 2, it has been surprisingly found that alcohols can be efficiently and quickly recovered by contacting a concentrated aqueous strong acid solution thereof 104 (herein termed the "acid/alcohol feedstream") with an effective amount of an extraction solvent 166 selected from the group consisting of alicyclic and acyclic alkyl carboxylic acids having from 6 to 20 carbon atoms per molecule. The carboxylic acids which are employed as extraction solvents 166 in the process of this invention therefore comprise at least one member selected from the group consisting of carboxylic acids of the formula:

$$R-\overset{\overset{\displaystyle O}{\|}}{C}-OH \qquad (I)$$

wherein R is an alicyclic or acyclic alkyl group having from 5 to 19 carbon atoms. When "R" is acyclic alkyl, the alkyl group can be straight or branched chain. The "R" group can be substituted with nonreactive groups such as fluoro and chloro. Examples of such "R" groups are pentyl, hexyl, decyl, dodecyl, tetradecyl, undecyl, 2-ethylhexyl, cyclohexyl, cyclooctyl and fluoro- and chloro- substituted derivatives of the foregoing.

A preferred class of carboxylic acid extraction solvents for use in this invention comprise saturated acids, and especially saturated hindered acids wherein the carboxyl groups are sterically blocked or hindered. The discussion of steric hinderance may be found in Newman, Steric Effects in Organic Chemistry, 1956, pp. 204–207. Generally, steric hindrance results from the presence of tertiary or quaternary alpha, beta or gamma carbon atoms in the acid, increasing substitution leading to increased hindrance. Steric hindrance has been observed to tend to prevent esterification of the carboxylic acid with the alcohol.

A class of particularly preferred sterically hindered carboxylic acids are the neo acids ("neo" is used to denote a carbon atom that is bonded to four other carbon atoms, e.g., as in neo-hexanoic acid, i.e. 2,2-dimethyl butanoic acid). Thus, the preferred neo-acids can be represented by members selected from the group consisting of acids having the formula (II):

$$R^2-\overset{\overset{\displaystyle R^1}{|}}{\underset{\underset{\displaystyle R^3}{|}}{C}}-\overset{\overset{\displaystyle O}{\|}}{C}-OH \qquad (II)$$

wherein $R^1$, $R^2$ and $R^3$ are the same or different and are independently selected from the group consisting of cyclic and alicyclic alkyl of from 1 to 16 carbon atoms, with the proviso that the neo acid contains a total of from 6 to 20 carbon atoms per molecule, and preferably from 7 to 15 carbon atoms per molecule. The alicyclic alkyl groups can be straight or branched. A preferred class of neo acids are those wherein, referring to formula II above $R^1$ and $R^2$ are preferably each alkyl radicals having from 1 to 3 carbon atoms per radical and $R^3$ is preferably alkyl having from 1 to 6 carbon atoms, provided that the neo-acid has a total of at least 6, and preferably at least 7, carbon atoms per molecule.

Some typical examples of neo acids are 2,2-dimethyl butanoic acid; alpha, alpha-dimethyl cyclohexyl acetic acid; alpha, alpha-dimethyl octanoic acid; 1-methyl-4-propylcyclohexane-1-carboxylic acid; and the like.

Commercial neo-acids which comprise a mixture of isomers, all with the neo structure (formula II), such as neo-heptanoic acid, neo-octanoic acid, neononanoic acid, neo-decanoic acid and neo-tridecanoic acid, are especially useful and preferred in the process of this invention. The preparation and properties of the commercial carboxylic acids are described in N. Fefer and A. Rutkouski, *J. Am. Oil Chemists Soc.,* 45, 5 (1968). Neo acids can also be prepared by the well known Koch process from carbon monoxide, water and type II, III, IV or V olefins as described by H. Koch in Brenntstaff Chem., 36, 321 (1955). Further details on methods for making neo acids can be found in British Pat. No. 998,974 and U.S. Pat. No. 3,349,107, all of which are hereby incorporated by reference. Neo acids are often made from branched chain olefin feedstocks which are random isomeric mixtures in regard to the position of the olefinic bond. These acids are thus random isomeric mixtures of neo acids. These neo acids are suitable in their isomeric forms, or any suitable mixtures thereof may be employed.

The carboxylic acid extraction solvent of this invention may be used alone or as mixtures with a cosolvent for the selected alcohol, such as a $C_{10}$ to $C_{20}$ paraffinic hydrocarbon, a $C_7$ to $C_{12}$ aromatic hydrocarbon, or a $C_1$ to $C_{10}$ alkyl ester of a $C_4$ to $C_{15}$ monocarboxylic acid. When used, such additional cosolvents will be generally employed in such mixtures in an amount of less than about 45 wt. % of the carboxylic acid/cosolvent mixture. In particular, it has been observed that the carboxylic acid extraction solvents of this invention, when contacted with alcohol and concentrated aqueous acid, will form the corresponding carboxylic ester of the alcohol, albeit at a rate which varies depending on the particular carboxylic acid extraction solvent selected for use. For example, steric hindrance in the carboxylic acid, especially the neo structures (Structure II) will tend to reduce the rate and equilibrium constant of the esterification reaction. Eventually, the thus-formed ester of the carboxylic acid extraction solvent will build up to approximately a steady-state concentration in the continuous process in which the carboxylic acid extraction solvent is repeatedly recycled to extract additional quantities of alcohol from the alcohol-containing concentrated aqueous acid feedstream (as will be described in more detail below).

The selected carboxylic acid extraction solvent of this invention may be contacted with the acid/alcohol feedstream in extraction zone 160 in any convenient manner, including continuous, semi-continous or batchwise operations, in a single or in multiple extraction stages. The concentration of the strong acid (e.g., sulfuric acid) in acid/alcohol feedstreams 104 (herein termed the "acid strength" or "A.S.") to be so contacted, can vary widely and will typically range from about 40 to 80 wt. % sulfuric acid, preferably from about 50 to 65 wt. % sulfuric acid when a neo acid is employed as the extracting solvent. As used herein, the acid strength in the acid/alcohol feedstream is defined herein on an organic free basis, as follows (using $H_2SO_4$ as the acid for purposes of illustration)

$$A.S. = \frac{W_1 + \left[\frac{M_1 \times W_4}{M_1 + M_5}\right]}{W_1 + W_2 + \left[\frac{18W_3}{M_3}\right] + \left[\frac{M_1 \times W_4}{M_1 + M_5}\right]} \times 100$$

wherein $W_1$ is the weight of strong acid, $W_2$ is the weight of $H_2O$, $W_3$ is the weight of alcohol, $W_4$ is the weight of the mono alkyl ester of the strong acid, $M_3$ is the molecular weight of the alcohol, $M_1$ is the molecular weight of the strong acid, and $M_5$ is the molecular weight of the olefin. Also, the concentrations of the alcohol and alkyl ester in the stream 104 can vary widely, and the saturated monoalcohol concentration will generally range from about 5 to 50 wt. % and preferably from about 10 to 40 wt. % and the saturated alcohol alkyl ester of the strong acid will generally range from about 1 to 15 wt. %, and preferably from about 1 to 5 wt. %, of total alkyl ester (mono- and di-alkyl ester).

The amount of carboxylic acid extraction solvent which is used to contact the acid/alcohol feedstream can also vary widely. Preferably, the carboxylic acid extraction solvent of this invention and the acid/alcohol feedstream are contacted in zone 160 in a ratio of from about 0.3 to 5 parts by weight of the carboxylic acid per part by weight of the acid/alcohol feedstream.

The temperature and pressure in zone 160 in which such extraction is performed using the carboxylic acid solvents of this invention is not critical, and will vary widely depending upon the particular carboxylic acid solvent employed, the degree of efficiency of removal desired for the alcohol, phase settling time desired, and other factors. Generally, however, temperature within the range from about 25° to 100° C., preferably from about 25° to 80° C., can be used, and the pressure can be atmospheric, subatmospheric or superatmospheric, with pressures of from about 2 to 100 psig being typically suitable. Similarly, the time for the contacting of the selected carboxylic acid solvent of this invention and the acid/alcohol feedstream is not critical and can vary widely, but will typically fall within the range of from about 0.1 to 6 hours.

Finally, the process of this invention can employ as extraction zone 160, in which the extraction with carboxylic acid solvent is carried out, any of the conventional equipment which are employed for liquid-liquid extractions. For example, the solvent and the acid/alcohol feedstream can be introduced as a combined stream into a stirred tank, and the resulting liquids passed to a settling drum from which the light phase (alcohol solvent phase) and the heavy phase (lean acid-/alcohol phase) can be recovered. Alternatively, the contacting zone can comprise a static plate extraction column (either packed or trayed column), a reciprocating plate column (such as the KARR® columm), stirred columns (such as YORK-SCHIEBEL® columns) and the like.

In the process of this invention, water may be added to the acid/alcohol feedstream 104 in order to provide the water of hydration for formation of the selected alcohol from alkyl ester corresponding to the alcohol. This water can be introduced via stream 112 into the conduit carrying the acid/alcohol feedstream 104 as illustrated, or the water can be introduced into zone 160 itself. Generally, from about 0.04 to 0.4 parts by weight of water are added per part by weight of the acid/alcohol feedstream.

An alcohol-rich carboxylic acid extract stream 162 can be thus separated and recovered as the light phase from extraction zone 160, either directly from zone 160 (as illustrated) or following treatment of a two-phase mixture removed from the contacting zone to a conventional phase separation vessel. This alcohol-rich carboxylic extract 162 generally contains from about 5 to 20 wt. % alcohol and from about 95 to 45 wt. % of the carboxylic acid solvent. The alcohol-rich carboxylic acid extract 162 will only contain a minor proportion of water, preferably less than about 2 wt. % water, more preferably less than about 1 wt. % water, and most preferably less than about 0.3 wt. % water. In addition, it has been found that the carboxylic acid extraction solvents of this invention permit recovery of such a alcohol-rich stream without, at the same time, contamination with significant amounts of the strong acid or alkyl ester of the strong acid. Generally, the alcohol-rich carboxylic acid extract 162 recovered from the contacting zone contains less than about 1 wt. %, most preferably less than about 0.3 wt. %, of such alkyl esters and is substantially free of the strong acid, that is, contains less than 0.1 wt. % and most preferably less than 0.01 wt. %, of the strong acid (e.g., $H_2SO_4$).

A second phase 168 can also be recovered, again either directly or indirectly, from the extraction zone 160 as the heavy phase and comprises a mixture of water, strong acid and alkyl moieties, either as the monoester or di-ester of the strong acid or the alcohol, or mixtures thereof, enriched in the strong acid. This separated strong acid-enriched phase 168 can be recycled to an olefin absorbing zone 110, after addition of make-up strong acid 105, if required. Generally, this strong acid phase 168 separated from the extraction zone 160 will contain strong acids in an acid concentration of at least 1 wt. %, and preferably from about 2 to 10 wt. % greater than the acid concentration of the strong acid in the diluted acid/alcohol feedstream 117 passed to extraction zone 160.

Preferably, the extraction process of this invention is performed by continuously passing the acid/alcohol feedstream 117 and the carboxylic acid extraction solvent 166 to the extraction zone 160 countercurrently, and at flow rates such that the strong acid phase, that is the acid/alcohol feedstream 117, is the discontinuous phase and is introduced to the upper portion of the extraction tower 160, with the extraction solvent phase comprising the continuous phase. It has been found that such an embodiment greatly reduces the time required for phase separations to occur during the extraction.

The manner in which the acid/alcohol feedstream 104 is formed is not critical to this invention. When feedstream 104 is formed by absorption of olefin into a strong acid, any of the prior art methods and absorption apparatus can be used, as described above.

Therefore, in one embodiment of the process of this invention, feedstream 104 can be formed by passing an olefin stream 102 to conventional absorbing zone 110 for countercurrent contact therein with a concentrated strong acid stream 106. Olefin 102 can comprise any of the above mentioned aliphatic olefins having from 3 to 8 carbon atoms per molecule, and particularly olefins having 3 or 4 carbon atoms per molecule. Similarly, the identity and concentration of the strong acid in acid stream 106, the temperature and pressure and other conditions used in absorbing zone 110 correspond to those which have been discussed earlier. Therefore, when the olefin comprises propylene, and the strong acid is sulfuric acid, stream 106 will generally comprise sulfuric acid of an acid strength of from about 45 to 99%, more preferably from about 50 to 80%, and when the olefin 102 comprises butylene or higher olefin feeds, stream 106 will generally comprise sulfuric acid of an acid strength of from about 45 to 85 wt. % and more preferably from about 55 to 80 wt. %. Generally, a temperature of from about 20° to 150° C. and a pressure of from about 60 to 500 psig will be used.

Further, any of the above-discussed strong acids can be employed, and such acids will generally comprise a strong organic or inorganic acid which is miscible with water and which is characterized by dissociation constants ("pK" values) in aqueous solutions of less than about 3.5. Examples of suitable inorganic olefin hydration acids are hydrofluoric acid, hydroiodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like.

Unabsorbed gases are withdrawn from the upper portion of absorbing zone 110 via conduit 107 and can be recycled if desired to conduit 102 or subjected to conventional scrubbing/washing treatment, as with caustic solutions.

Therefore, the alcohols recovered by the process of this invention comprise the alcohol corresponding to the olefin(s) fed to the absorbing zone 110, and generally comprise saturated mono-alcohols having from 3 to 8 carbon atoms per molecule, and preferably having 3 or 4 carbon atoms per molecule. Examples of such alcohols are n-butanol, iso-butanol, sec-butanol, tert-butyl alcohol, n-propanol, iso-propanol, pentanols, hexanols and octanols.

As used herein, the term "extract saturation" (i.e., "E.S." values) of strong acid solutions, containing alcohol and/or alkyl ester of the strong acid, is defined by the expression (III):

$$E.S. = \frac{X^1}{X^A} \quad \text{(III)}$$

wherein $X^1$ is the mole fraction of alcohol (and alcohol-equivalents represented by the alkyl esters) absorbed in the liquid and $X^A$ is the mole fraction in the liquid of the strong acid and strong acid moieties of the strong acid esters.

The manner in which the alcohol is extracted from the sulfuric acid/alcohol feedstream using such carboxylic acid extraction solvents is more particularly described in co-pending application Attorney's Docket No. CS-342, entitled "Improved Process for Recovering Alcohols from Sulfuric Acid Streams", which is hereby incorporated by reference.

The alcohol-rich carboxylic acid extract 162 can then be treated by the method of the present invention for recovery of the alcohol therefrom and for recovery and separation of the carboxylic acid solvent for recycle, if desired, to the extraction zone 160 in order to extract additional quantities of alcohol therein. According to the alcohol separation method of this invention, the alcohol-rich carboxylic acid extract 162 is passed to an alcohol vaporization zone wherein stream 162 is contacted with substantially anhydrous stripping vapors under conditions sufficient to form an overhead vapor product comprising at least a majority (that is, at least 50 wt. %) of the alcohol introduced to the alcohol vaporization zone with extract 162 (and preferably from about 70 to 95 wt. % of the thus-introduced alcohol) and substantially free of the carboxylic acid extraction solvent and to form a bottoms product comprising an alcohol depleted carboxylic acid stream which is preferably suitable for recycle to an alcohol extraction zone, as described above.

The alcohol-rich carboxylic acid extract 162 can be treated in the alcohol vaporization zone by distillation, flashing or stripping using a substantially anhydrous gas which is substantially inert to the alcohol and to the carboxylic acid under striping conditions. Suitable stripping gases include $N_2$, olefins and saturated hydrocarbons, with mono-olefins of from 2 to 8 carbon atoms and alkanes of from 2 to 8 carbon atoms being preferred. Therefore, the alcohol vaporization zone can comprise one or more flashing zones, distillation zones, gas stripping zones or combinations of the foregoing.

The introduction of steam into the alcohol-carboxylic acid mixture is preferably avoided, since it has been found that the carboxylic acid's affinity for water is greatly increased in the absence of sulfuric acid. Thus, it has been found that if open steam distillation or stripping were used, while alcohol vapors could be stripped overhead, the bottoms stream from such a steam stripper would comprise an aqueous carboxylic acid mixture which when recycled to the liquid/liquid extraction zone would tend to build water in the system, and thereby decrease the efficiency of reconcentration of sulfuric acid as discussed above. Since low selectivity for water absorbtion by the carboxylic acid solvent in the liquid/liquid extraction zone 160 is critical, the introduction of steam or water vapor into the alcohol vaporization zone via open steam distillation or steam stripping should be avoided. Also, it has been found that alcohol-water-carboxylic acid extraction solvent mixtures can present settling problems in recovering alcohol and/or the carboxylic acid solvent therefrom, when such steam distillation or steam stripping methods are attempted.

According to one embodiment of the process of this invention, illustrated in FIG. 2, the separated alcohol-enriched carboxylic acid extract phase 162 is heated (e.g., using heat exchanger 167) to a temperature of from about 0° to 100° C. higher than the temperature employed in extraction zone 160, and the resulting heated alcohol-enriched stream 165 is flashed into a vapor/liquid separation zone 170 (such as a suitable vapor/liquid separating drum) at a lower pressure in order to effect vaporization of at least a majority of the alcohol and thereby permit recovery of alcohol vapors 172 from this flashing zone 170. A lean solvent phase comprising the carboxylic acid extraction solvent can be withdrawn from flashing zone 170 via conduit 166 and recycled to extraction zone 160, after addition of make-up carboxylic acid extraction solvent 169, if required. (Alternatively, if the pressure in flashing zone 170 is sufficiently low, the use of heater 167 can be eliminated and stream 162 can be passed to zone 170 directly.)

The conditions of temperature and pressure which are employed in flashing zone 170 for alcohol recovery will vary widely depending upon the alcohol to be recovered, the particular carboyxlic acid extraction solvent which is used, and other factors. Generally, however, flashing zone 170 should employ a temperature of from about 30° to 200° C., preferably from about 60°to 150° C., (as determined in flashfeed stream 165) for recovery of alcohols of from 3 to 8 carbon atoms. Preferably, the carboxylic acid extraction solvent which is used in this invention possesses a normal boiling point of at least about 100° C., more preferably at least about 140° C., greater than the normal boiling point of the alcohol in order to permit more efficient separation of the alcohol vapors 172 without, at the same time, contaminating the thus-separated vapors with significant quantities of the carboxylic acid solvent itself.

The conditions of pressure which are used in flashing zone 170 will, of course, have an effect on the necessary temperatures to recover the alcohol by flashing, but generally, the pressure in the flashing zone 172, will range from about 2 to 150 psia, and more preferably from about 5 to 50 psia.

According to another embodiment of the process of this invention, the alcohol-rich carboxylic acid extract 162 can be distilled in a conventional distillation column (not shown) provided with a reboiler, whereby at least a portion of the bottoms product is reboiled by indirect heat exchange with a heating fluid (e.g., steam) and the thus-heated stream is reintroduced into the lower portion of the distillation column (typically below the feed point in the column to which the alcohol-rich carboxylic acid extract liquid stream is introduced). The alcohol vapors are withdrawn as the overhead product, and if desired can be at least partially condensed to form a liquid reflux to the upper portion of the column.

Figure 3:
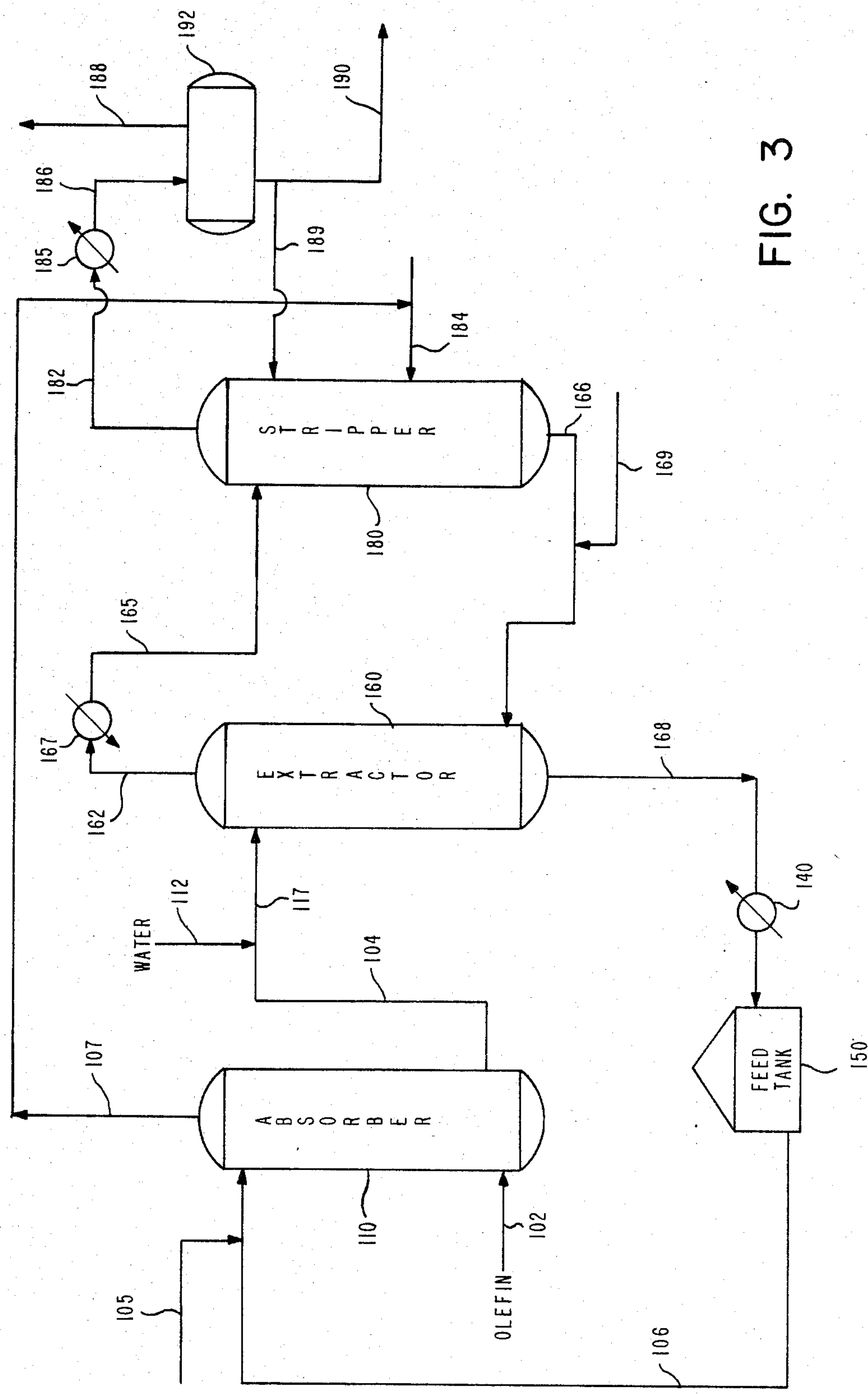
FIG. 3 is a diagrammatic illustration of a second embodiment of the cyclic process of this invention.

According to yet another and preferred embodiment of the process of this invention, illustrated in FIG. 3, the alcohol-rich carboxylic acid extract 162 is passed to stripping zone 180 (optionally, after heating stream 162 in heater 167, as described above) wherein the extract liquid is stripped by means of a stripping gas 184 which is introduced to the lower portion of stripping zone 180, to form a vaporous overhead product stream 182 and a liquid bottoms product 166. Overhead product 180 which comprises at least a majority of the feed alcohol, as described above, and which also contains the stripping gas, can be cooled in cooler 185 to condense the alcohol vapors. The resulting gas/liquid stream 186 can be passed to a vapor/liquid separation drum 192, to permit separation and withdrawal of uncondensed vapors 188, comprising the stripping gas, and a liquid alcohol stream 190, which can be withdrawn and subjected to further purification, if desired. A portion of liquid alcohol stream 190 can be passed via conduit 189 as liquid reflux to stripping zone 180.

The bottoms product 166 comprises the alcohol-depleted carboxylic acid stream and can be recycled to extractor 160 (with the addition of make-up carboxylic acid via conduit 169, as required) for extraction of additional quantities of the alcohol.

As described earlier, stripping gas 184 comprises a substantially anhydrous gas which is substantially inert to the alcohol and to the carboxylic acid under stripping conditions. Suitable stripping gases include $N_2$, mono-olefins of from 2 to 8 carbon atoms and alkanes of from 2 to 8 carbon atoms. Preferably, stripping gas 184 comprises a mono-olefin, alkane or mixture thereof corresponding to the mono-alcohol sought to be stripped from extract 162. A particularly preferred source of such an olefin stripping gas 184 in the off-gas stream 107 removed from the overhead of olefin absorbing zone 110.

The conditions of temperature and pressure which are employed in stripping zone 180 for alcohol recovery will vary widely depending upon the alcohol to be recovered, the particular carboxylic acid extraction solvent which is used, and other factors. Generally, however, stripping zone 180 will employ a temperature of from about 30° to 200° C., preferably from about 60° to 150° C. (as determined in the feedstream 165), for recovery of mono alcohols of from 3 to 8 carbon atoms. Preferably, the carboxylic acid extraction solvent which is used in this invention possesses a normal boiling point of at least 100° C., more preferably at least about 140° C., greater than the normal boiling point of the alcohol in order to permit more efficient separation of the alcohol vapors 182 without, at the same time, contaminating the thus-separated vapors with significant quantities of the carboxylic acid solvent itself.

The conditions of pressure which are used in stripping zone 180 can also vary widely but will generally range from about 2 to 150 psia, and more preferably from about 5 to 50 psia.

The alcohol-depleted carboxylic acid stream 166 formed as described above preferably contain the carboxylic acid in a concentration at least as great as (and more preferably from about 1.01 to 1.15 times greater than) the concentration of the carboxylic acid in the alcohol-rich carboxylic acid extract stream 162 which was treated in the alcohol vaporization zone according to the process of this invention. In addition, alcohol-depleted carboxylic acid stream 166 preferably contains water in a concentration of less than about 1 wt. %, and more preferably less than about 0.5 wt. %, most preferably less than about 0.2 wt. %.

The overhead alcohol vapors (e.g., 162 or 182) withdrawn from the vaporization zone of this invention preferably contain less than about 2 wt. % of the carboxylic acid extraction solvent, and comprise at least 50 wt. % (and preferably from about 70 to 95 wt. %) of the liquid alcohol feed to the alcohol vaporization zone.

It will be understood from the foregoing that the anhydrous stripping vapors employed herein to separate the alcohol comprise either (1) internally generated vapors when either the aforedescribed flashing method or the rebvoiling distillation method is employed or (2) a separate stripping gas, e.g., the olefin vapors withdrawn from an olefin extractor 110, and that such vapors/gases are deemed herein to be "anhydrous" if they do not contain water not introduced to the vaporization zone with the liquid alcohol feed thereto. For example, if such internally generated stripping vapor, are generated in a reboiled distillation column, the bottoms product which is reboiled to provide heat to the distillation column may contain water in an amount corresponding to the vapor/liquid equilbria of the distillation system's last (lowest) theoretical vapor/liquid contacting stage. Therefore, the reintroduction of such reboiled steam into the distillation column will not introduce water into the column in amounts in excess of that passed to the column with the liquid alcohol feed. Similarly, when the stripping vapors are generated by flashing, a portion of the water content of the liquid alcohol feed will also generally vaporize, but such water is indigeneous and the resulting vapors are nevertheless "anhydrous" stripping vapors under the above definition. Finally, if a separate stripping gas 184 is used, preferably this gas stream is substantially water free, that is contains less than about 10 wt. % water, and more preferably less than about 5 wt. % water.

Gas chromatograph analyses were performed in the Examples using a known amount of methyl isobutyl carbonyl (MIBC) as internal standard. The sample was injected into a HP 5880A GC with a 60 meter SE 30 capillary column. The oven temperature was initially at 40° C. for 4 minutes then temperature program at 5°/min to 200° C. The injection port and detector temperatures were 225° and 330° C., respectively. Water content was analyzed using a ⅛"×10' Porapak N column at 175° C. (isothermal) column temperature with thermo-conductivity detector.

EXAMPLE 1

A mixture of butene, secondary butyl ether ("SBE"), secondary butyl alcohol ("SBOH") and neo-decanoic acid ("NDA") was prepared in the selected amounts and continuously passed as feed to the eighth tray of a ten-tray distillation column (1 inch Oldershaw). A preheated stripping gas, comprising butenes, was continuously charged below the first tray of the column. The liquid feed thus passed to the extraction unit was preheated to the selected temperature. The distillation column was provided with a vacuum jacket, and the upper portion of the column was provided with a partial condenser to partially condense the overhead product and a phase separator to separate the condensed sec-butyl alcohol from uncondensed gases, including the butenes. The bottoms product comprised the neo-decanoic acid depleted in alcohol. The liquids thereby obtained were each analyzed by gas chromotography and nuclear magnetic resonance for component identification. The data data thereby obtained are set forth in Table I.

The partially condensed liquids obtained from the overhead products in this distillation was found to contain 11.05 wt. % dissolved butenes, 82.21 wt. % SBOH, 0.22 wt. % SBE, 5.37 wt. % water and 1.15 wt. % NDA.

EXAMPLE 2

The procedure of Example 1 is repeated employing the conditions set forth in Table II.

The recovered liquid condensate, separated from the overhead product stream, was found to contain 10.12 wt. % butenes, 82.78 wt. % SBOH, 0.25 wt. % SBE, 4.87 wt. % water, and 1.98 wt. % NDA.

EXAMPLE 3

The procedure of Example 1 is repeated employing the conditions set forth in Table III.

The recovered liquid condensate, separated from the overhead product stream, was found to contain 13.31 wt. % butenes, 80.69 wt. % SBOH, 0.28 wt. % SBE, 4.64 wt. % water, and 1.08 wt. % NDA.

EXAMPLE 4 FOR COMPARISON

The procedure of Example 1 is repeated except that the stripping gas containing butenes also contains water, in a concentration of about 7.4 wt. %.

The results thereby obtained are set forth in Table IV. These results indicate that the liquid condensate following partial condensation contained 2.18 wt. % butenes, 82.08 wt. % SBOH, 9.96 wt. % water, and 5.77 wt. % NDA. This indicates the significantly increased water concentrations in the desired SBOH product and the increased NDA content of this SBOH product stream, which results when the stripping gas contains significant levels of water.

EXAMPLE 5 FOR COMPARISON

A series of runs were conducted using the procedure of Example 1 except the stripping gas comprised steam, using the selected steam feed pressure and temperatures indicated in Tables V and VI below.

The data thereby obtained illustrate the undesirability of recovering the secondary butyl alcohol by steam stripping. In these runs a significant concentration of the NDA solvent was noted in the overhead product. In addition, it was observed that the bottoms product withdrawn from the stripping column contained high amounts of water and resulted in a two-phase bottoms product which had very poor settling qualities. The organic phase of this bottoms product comprised the NDA solvent layer; However, its high water content rendered that the phase undesirable for recycle to an extraction process wherein the SBOH is desired to be extracted using the NDA from an aqueous SBOH-sulfuric acid solution, wherein dilution of the resulting alcohol-depleted sulfuric acid is desirably avoided. Thus, although high alcohol recoveries can be achieved using steam stripping, as is illustrated by Table VI, the water content of the separated bottoms product organic phase is unacceptably great.

TABLE I

Continuous Olefin Stripping(1)
Solvent = Neo-Decanoic Acid

| | NDA/SBOH Feedstream(2) | | Stripping Gas | | Overhead | Product(3) | Bottoms | Product |
|---|---|---|---|---|---|---|---|---|
| Components | GMS | moles/hr. | GMS | Moles/hr. | GMS | Moles/hr. | GMS | Moles/hr. |
| Butene | 46.756 | 1.67 | 118.8 | 4.24 | 110.23 | 3.937 | 55.32 | 1.976 |
| SBE | 1.709 | 0.026 | 0 | 0 | 0.157 | 0.0024 | 1.552 | 0.0238 |
| SBOH | 93.513 | 2.53 | 0 | 0 | 59.095 | 1.597 | 34.417 | 0.93 |
| Water | 5.860 | 0.651 | 0 | 0 | 3.849 | 0.428 | 2.011 | 0.223 |
| NDA | 1072.9 | 12.476 | 0 | 0 | 0.836 | 0.0096 | 1072.1 | 12.466 |
| Total | 1220.8 | 8.675 | 118.8 | 4.24 | 174.17 | 5.97 | 1180.8 | 15.62 |

(1)Stripping gas to liquid feed: 0.0973:1 wt:wt; 1.270 4:1 vol:vol reflux ratio = 0.2.

(2)Specific gravity, 25° C. = 0.88

Temperatures: stripping gas feed = 92° C.; liquid feed = 120° C.; overhead product vapor = 70° C.; liquid feed tray vapor = 107° C.; stripping tray vapor = 115° C.; bottoms product liquid = 74° C.

(3)Partial condensation of overhead product provided 102.27 gms of gas and 71.9 gms of liquid product containing 82.2 wt. % SBOH, representing 63.2 wt. % recovery of feed alcohol.

TABLE II

Continuous Olefin Stripping(1)
Solvent = Neo-decanoic acid

| | NDA/SBOH Feedstream(2) | | Stripping Gas | | Overhead | Product(3) | Bottoms | Product |
|---|---|---|---|---|---|---|---|---|
| Components | GMS | moles/hr. | GMS | Moles/hr. | GMS | Moles/hr. | GMS | Moles/hr. |
| Butene | 49.156 | 1.755 | 118.8 | 4.243 | 115.81 | 4.14 | 52.141 | 1.862 |
| SBE | 1.556 | 0.0238 | 0 | 0 | 0.215 | 0.0032 | 1.341 | 0.0206 |
| SBOH | 97.015 | 2.622 | 0 | 0 | 73.583 | 1.99 | 23.432 | 0.633 |
| Water | 5.0583 | 0.562 | 0 | 0 | 4.325 | 0.48 | 0.733 | 0.0814 |
| NDA | 1144.2 | 13.305 | 0 | 0 | 1.761 | 0.020 | 1142.4 | 13.284 |
| Total | 1297 | 18.268 | 118.8 | 4.243 | 195.7 | 6.63 | 1228.2 | 15.882 |

(1)Stripping gas to liquid feed: 0.9915:1 wt:wt; 1.2245:1 vol:vol Reflux ratio = 0.2
(2)Specific gravity, 25° C. = 0.88
Temperatures: stripping gas feed 91° C.; liquid feed = 125° C.; overhead product vapor = 86° C.; liquid feed tray vapor = 113° C.; stripping tray vapor = 118° C.; bottoms product liquid = 74° C.
(3)Partial condensation of overhead product provided 106.8 gms of gas and 88.9 gms of liquid product containing 82.8 wt. % SBOH, representing 75.85 wt. % recovery of feed alcohol.

TABLE III

Continuous Olefin Stripping(1)
Solvent = Neo-decanoic acid

| | NDA/SBOH Feedstream(2) | | Stripping Gas | | Overhead | Product(3) | Bottoms | Product |
|---|---|---|---|---|---|---|---|---|
| Components | GMS | moles/hr. | GMS | Moles/hr. | GMS | Moles/hr. | GMS | Moles/hr. |
| Butene | 38.36 | 1.37 | 118.8 | 4.242 | 122.3 | 4.37 | 34.78 | 1.24 |
| SBE | 1.534 | 0.0236 | 0 | 0 | 0.179 | 0.0026 | 1.355 | 0.0208 |
| SBOH | 77.44 | 2.093 | 0 | 0 | 53.012 | 1.433 | 24.43 | 0.660 |
| Water | 4.092 | 0.455 | 0 | 0 | 3.049 | 0.3386 | 1.043 | 0.1158 |
| NDA | 901.56 | 10.48 | 0 | 0 | 0.717 | 0.0082 | 900.85 | 10.475 |
| Total | 1023 | 14.424 | 118.8 | 4.242 | 179.34 | 6.154 | 963.8 | 12.51 |

(1)Stripping gas to liquid feed: 0.1161:1 wt:wt; 1.5340:1 vol:vol Reflux ratio = 1
(2)Specific gravity, 25° C. = 0.88
Temperatures: stripping gas feed = 92° C.; liquid feed = 125° C.; overhead product vapor = 68° C.; liquid feed tray vapor = 99° C.; stripping tray vapor = 113° C.; bottoms product liquid = 74° C.
(3)Partial condensation of overhead product provided 112.64 gms of gas and 66.7 gms of liquid product containing 80.7 wt. % SBOH, representing 69.5 wt. % recovery of feed alcohol.

TABLE IV

Continuous Olefin Stripping(1)
Solvent = Neo-decanoic Acid

| | NDA/SBOH Feedstream(2) | | Stripping Gas | | Overhead | Product(3) | Bottoms | Product |
|---|---|---|---|---|---|---|---|---|
| Components | GMS | moles/hr. | GMS | Moles/hr. | GMS | Moles/hr. | GMS | Moles/hr. |
| Butene | 42.06 | 1.502 | 118.9 | 4.25 | 160.86 | 5.74 | 0.099 | 0.0034 |
| SBOH | 85.54 | 2.32 | 0 | 0 | 63.03 | 1.70 | 22.81 | 0.909 |
| Water | 0 | 0 | 9.502 | 1.06 | 7.645 | 0.85 | 1.856 | 0.0048 |
| NDA | 730.49 | 8.49 | 0 | 0 | 14.436 | 0.051 | 726.06 | 1.934 |
| Total | 858.4 | 12.32 | 128.4 | 5.30 | 235.97 | 8.35 | 795.2 | 9.27 |

(1)Stripping gas to liquid feed: 0.1495:1 wt:wt; 0.2231:1 vol:vol Reflux ratio = zero.
(2)Specific gravity, 25° C. = 0.88
Temperatures: stripping gas feed = 82° C.; liquid feed = 125° C.; overhead product vapor = 78° C.; liquid feed tray vapor = 107° C.; stripping tray vapor = 100° C.; bottoms product liquid = 74° C.
(3)Partial condensation of overhead product provided 159.17 gms of gas and 76.8 gms of liquid product containing 82.08 wt. % SBOH, representing 73.4 wt. % recovery of feed alcohol.

TABLE V

Continuous Olefin Stripping (1)
Solvent = Neo-decanoic acid

| | NDA/SBOH Feedstream(2) | | Stripping Gas | | Overhead | Product(3) | Bottoms | Product |
|---|---|---|---|---|---|---|---|---|
| Components | GMS | moles/hr. | GMS | Moles/hr. | GMS | Moles/hr. | GMS | Moles/hr. |
| Butene | 0 | 0 | 0 | 0 | 0 | 0 | 0 | 0 |
| SBE | 0 | 0 | 0 | 0 | 0 | 0 | 0 | 0 |
| SBOH | 22.7 | 0.614 | 0 | 0 | 16.2 | 0.438 | 6.5 | 0.176 |
| Water | 0.6 | 0.067 | 33.0 | 3.67 | 14.6 | 1.62 | 19.6 | 2.178 |
| NDA | 253.8 | 2.95 | 0 | 0 | 0.4 | 0.005 | 250.3 | 2.910 |
| Total | 277.1 | 3.631 | 33.0 | 3.67 | 30.6 | 2.06 | 276.4 | 5.264 |

(1)Reflux ratio = Zero. Steam feed pressure = 3.3 psig
(2)Temperatures: stripping gas feed = 130° C.; liquid feed = 110° C.; overhead product vapor = 88° C.; liquid feed tray vapor = 104° C.; bottoms product liquid = 118° C.
(3)Partial condensation of overhead product provided liquid containing SBOH in an amount representing 71.4 wt. % recovery of feed alcohol.

TABLE VI

Continuous Olefin Stripping(1)
Solvent = Neo-decanoic acid

| Components | NDA/SBOH Feedstream(2) GMS | NDA/SBOH Feedstream(2) moles/hr. | Stripping Gas GMS | Stripping Gas Moles/hr. | Overhead GMS | Product(3) Moles/hr. | Bottoms GMS | Product Moles/hr. |
|---|---|---|---|---|---|---|---|---|
| Butene | 0 | 0 | 0 | 0 | 0 | 0 | 0 | 0 |
| SBE | 0 | 0 | 0 | 0 | 0 | 0 | 0 | 0 |
| SBOH | 15.6 | 0.422 | 0 | 0 | 15.0 | 0.405 | 0.6 | 0.016 |
| Water | 0.6 | 0.067 | 46.5 | 1.26 | 37.2 | 4.13 | 9.9 | 1.1 |
| NDA | 173.7 | 2.02 | 0 | 0 | 0.7 | 0.008 | 174.1 | 2.02 |
| Total | 189.9 | 2.51 | 46.5 | 1.26 | 52.9 | 4.55 | 184.6 | 3.14 |

(1)Reflux ratio = zero. Steam feed pressure = 5.5 psig.
(2)Temperatures: stripping gas feed = 146° C.; liquid feed = 110° C.; overhead product vapor = 94° C.; liquid feed tray vapor = 99° C.; bottoms product liquid = 112° C.
(3)Partial condensation of overhead product provided liquid product containing SBOH in an amount representing 96.2 wt. % recovery of feed alcohol.

It will be obvious that various changes and modifications may be made without departing from the invention and it is intended, therefore, that all matter contained in the foregoing description shall be interpreted as illustrative only and not limitative of the invention.

What is claimed is:

1. An improved process for recovering alcohols from acid/alcohol feedstreams comprising aqueous strong acid solutions containing said alcohols which comprises (a) contacting said acid/alcohol feedstream in an extraction zone with an effective amount of an extraction solvent selected from the group consisting of alicyclic and acyclic carboxylic acids having from 6 to 20 carbons per molecule and mixtures thereof, for a time and under conditions sufficient to selectively extract said alcohol from said acid/alcohol feedstream and to form a first liquid phase comprising an alcohol-enriched carboxylic acid extract, and a second liquid phase comprising an aqueous strong acid raffinate depleted in alcohol, (b) introducing said alcohol-enriched carboxylic acid extract into an alcohol vaporization zone and contacting said extract therein with substantially anhydrous stripping vapors, in an amount and under conditions sufficient to form an overhead product comprising at least a majority of said alcohol passed to said vaporization zone and an alcohol-depleted carboxylic acid extraction solvent liquid, (c) recovering said alcohol vapors from said vaporization zone, and (d) recycling said alcohol-depleted carboxylic acid extraction solvent to said extraction zone.

2. The process of claim 1 wherein said vaporization zone comprises a flashing zone and wherein said substantially anhydrous stripping vapors are formed therein by flashing said alcohol-enriched carboxylic extract into said flashing zone at a reduced pressure.

3. The process of claim 1 wherein said substantially anhydrous stripping vapors comprise at least one gas selected from the group consisting of nitrogen, olefins of 3 to 8 carbon atoms and alkanes of 3 to 8 carbon atoms.

4. The process of claim 1 wherein said alcohol comprises an aliphatic mono-alcohol having from 3 to 8 carbon atoms per molecule.

5. The process of claim 1 wherein said strong acid comprises sulfuric acid and wherein said acid/alcohol feedstream contains sulfuric acid in an acid strength of from about 40 to 80 wt. %.

6. The process of claim 1 wherein said acid/alcohol stream also contains an alkyl ester of said strong acid, wherein said alkyl moiety corresponds to said alcohol, and wherein said acid/alcohol feedstream is contacted with from about 0.04 to 0.4 parts by weight of water per part by weight of said acid/alcohol feedstream prior to said extraction zone.

7. The process of claim 1 wherein said alcohol-enriched carboxylic acid extract contains less than 1 wt. % of said strong acid.

8. The process of claim 1 wherein said alcohol-enriched carboxylic acid extract contains less than about 2 wt. % water.

9. The process of claim 1 wherein said aqueous strong acid raffinate depleted in alcohol contains said strong acid in an acid strength of at least 1 wt. % greater than the acid strength of said strong acid in said acid/alcohol feedstream.

10. The process of claim 7 wherein said strong acid acid strength in said raffinate is from about 2 to 7 wt. % greater than the acid strength of said acid/alcohol feedstream.

11. The process of claim 1 wherein said alcohol-enriched carboxylic acid extract contains said alcohol in a concentration of from 5 to 20 wt. %.

12. The process of claim 1 wherein said carboxylic acid extraction solvent comprises a neo-acid having from 6 to 20 carbons per molecule and mixtures thereof.

13. The process of claim 12 wherein said neo-acid is selected from the group consisting of acids of the formula

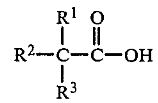

wherein $R^1$, $R^2$ and $R^3$ are the same or different and are independently selected from the group consisting of alkyl of from 1 to 16 carbon atoms, with the proviso that the neo acid contains a total of from 6 to 20 carbon atoms per molecule.

14. The process of claim 13 wherein $R^1$ and $R^2$ are each alkyl groups having from 1 to 3 carbon atoms per alkyl group, and $R^3$ is alkyl of from 1 to 6 carbon atoms.

15. The process of claim 1 wherein said carboxylic acid extraction solvent is employed in said extraction zone in an amount of from about 0.3 to 5 parts by weight per part by weight of said acid/alcohol feedstream.

16. The process of claim 2 wherein said flashing zone employs a temperature of from about 30° to 150° C. and a pressure of from about 2 to 150 psia.

17. The process of claim 16 wherein said carboxylic acid possesses a normal boiling point at about 100° C. greater than the normal boiling point of said alcohol.

18. The process of claim 1 wherein said alcohol-depleted carboxylic acid liquid contains said carboxylic acid in a concentration of at least as great as the concentration of said carboxylic acid in said alcohol-enriched carboyxlic acid extract.

19. The process of claim 1 wherein said alcohol-depleted carboxylic acid liquid is substantially free of water.

20. The process of claim 19 wherein said alcohol-depleted carboxylic acid liquid contains less than 1 weight percent water.

21. A process for recovering alcohols from acid/alcohol feedstreams comprising aqueous sulfuric acid solutions containing from 40 to 80 wt. % sulfuric acid and containing at least one saturated mono-alcohol having from 3 to 8 carbon atoms per molecule, which comprises (a) contacting said acid/alcohol feedstream in an extraction zone with an effective amount of an extraction solvent selected from the group consisting of neo-acids having from 6 to 20 carbon atoms per molecule for a time and under conditions sufficient to selectively extract said alcohol from said feedstream and to form a first liquid phase comprising an alcohol-enriched carboxylic acid extract containing said alcohol in a concentration of from about 5 to 20 weight percent and a second liquid phase comprising an aqueous sulfuric acid raffinate depleted in alcohol and having a sulfuric acid acid strength of at least 1 wt. % greater than the sulfuric acid acid strength in said acid/alcohol feedstream, (b) introducing said alcohol-enriched carboxylic acid extract to a vaporization zone and contacting said extract therein with a substantially anhydrous stripping gas comprising at least one member selected from the group consisting of $N_2$, olefins of from 3 to 8 carbon atoms and alkanes of from 3 to 8 carbon atoms, in an amount and under conditions sufficient to form an overhead product comprising at least a majority of said alcohol passed to said vaporization zone alcohol and an alcohol-depleted carboxylic acid extraction solvent liquid having a carboxylic acid concentration of from about 1.01 to 1.15 times greater than the concentration of said carboxylic acid in said alcohol-enriched carboxylic acid extract, (c) recovering said alcohol vapors, and (d) recycling at least a portion of said alcohol-depleted carboxylic acid extraction solvent liquid to said extraction zone.

22. The process of claim 21 wherein said neo-acid extraction solvent is employed in said extraction zone in an amount of from about 0.3 to 5 parts by weight of said neo-acid per part by weight of said partially diluted acid/alcohol feedstream.

23. The process of claim 21 wherein said alcohol-enriched carboxylic acid extract contains less than about 2 wt. % water and less than about 1 wt. % sulfuric acid.

24. The process of claim 21 wherein said alcohol comprises at least one member selected from the normal-butanol, iso-butanol, secondary-butanol and tertiary-butanol.

25. The process according to claim 21 wherein said neo acid comprises at least one acid selected from the group consisting of acids having the formula

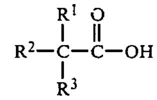

wherein $R^1$, $R^2$ and $R^3$ are the same or different and are independently selected from the group consisting of alkyl of from 1 to 16 carbon atoms, with the proviso that the neo acid contains a total of from 6 to 20 carbon atoms per molecule.

26. The process of claim 25 wherein said neo acid comprises at least one member selected from the group consisting of trimethylacetic acid; alpha, alpha dimethylcyclohexyl acetic acid; alpha, alpha-dimethyl octanoic acid; 1-methyl-4-propylcyclohexane-1-carboxylic acid; neo-heptanoic acid; neo-octanoic acid; neo-nonanoic acid; neo-decanoic acid; and neo-tridecanoic acid.

27. The process of claim 21 wherein said neo-acid extraction solvent is characterized by a normal boiling point of at least 100° C. greater than the normal boiling point of said alcohol.

28. The process of claim 21 wherein said alcohol-depleted carboxylic acid liquid is substantially free of water.

29. The process of claim 28 wherein said alcohol-depleted carboxylic acid liquid contains less than about 1 weight percent water.

30. The process of claim 21 wherein said overhead product contains alcohol in an amount corresponding to from about 70 to 95 weight percent of said alcohol introduced to said alcohol vaporization zone.

* * * * *